United States Patent
Soares Da Silva (10) Patent No.: US 9,855,277 B2
(45) Date of Patent: Jan. 2, 2018

(54) USE OF 5H-DIBENZ/B,F/AZEPINE-5-CARBOXAMIDE DERIVATIVES FOR TREATING FIBROMYALGIA

(75) Inventor: Patricio Manuel Viera Araújo Soares Da Silva, Oporto (PT)

(73) Assignee: BIAL—PORTELA & CA, S.A., S. Mamede Do Coronado (PT)

( * ) Notice: Subject to any disclaimer, the term of this patent is extended or adjusted under 35 U.S.C. 154(b) by 611 days.

(21) Appl. No.: 13/387,538

(22) PCT Filed: Jul. 27, 2009

(86) PCT No.: PCT/PT2009/000043
§ 371 (c)(1),
(2), (4) Date: May 8, 2012

(87) PCT Pub. No.: WO2011/014084
PCT Pub. Date: Feb. 3, 2011

(65) Prior Publication Data
US 2012/0214797 A1    Aug. 23, 2012

(51) Int. Cl.
*A61K 31/192* (2006.01)
*A61K 31/195* (2006.01)
(Continued)

(52) U.S. Cl.
CPC .................................. *A61K 31/55* (2013.01)

(58) Field of Classification Search
CPC . A61K 31/192; A61K 31/195; A61K 31/5513
(Continued)

(56) References Cited

U.S. PATENT DOCUMENTS

| 5,753,646 A * | 5/1998 | Benes et al. ............... 514/217 |
| 2004/0092504 A1* | 5/2004 | Benja-Athon ............... 514/217 |

(Continued)

FOREIGN PATENT DOCUMENTS

| WO | 9702250 A1 | 1/1997 |
| WO | 02092572 A1 | 11/2002 |

(Continued)

OTHER PUBLICATIONS

Ambrosio et al., Neurochemical Research, 2002;27(1/2)121-130.*
(Continued)

*Primary Examiner* — San-Ming Hui
(74) *Attorney, Agent, or Firm* — Finnegan, Henderson, Farabow, Garrett & Dunner, LLP (57) ABSTRACT

The use of 5H-dibenz/b,f/azepine-5-carboxamide derivatives for treating fibromyalgia. Useful 5H-dibenz/b,f/azepine-5-carboxamide derivatives include compounds of the formula (I):

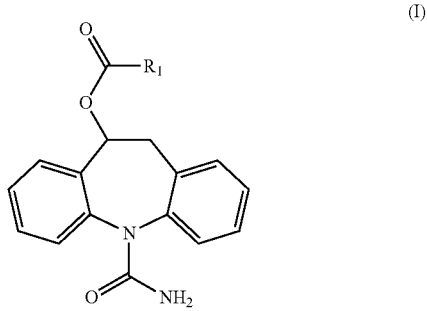

where $R_1$ is hydrogen, alkyl, halogenalkyl, aralkyl, cycloalkyl, cycloalkylalkyl, alkoxy, aryl, or pyridyl; the term
(Continued)

alkyl means a straight or branched hydrocarbon chain containing from 1 to 18 carbon atoms; the term halogen means fluorine, chlorine, bromine or iodine; the term cycloalkyl means an alicyclic saturated group with 3 to 6 carbon atoms; and the term aryl means an unsubstituted phenyl group or phenyl substituted by alkoxy, halogen or nitro group.

14 Claims, 2 Drawing Sheets

(51) Int. Cl.
    *A61K 31/5513*    (2006.01)
    *A61K 31/55*      (2006.01)
(58) Field of Classification Search
    USPC ........................................................ 514/217
    See application file for complete search history.

(56) References Cited

U.S. PATENT DOCUMENTS

| | | |
|---|---|---|
| 2006/0252745 A1 | 11/2006 | Almeida et al. |
| 2006/0252746 A1 | 11/2006 | Almeida et al. |
| 2010/0222327 A1 | 9/2010 | Almeida et al. |
| 2011/0319388 A1 | 12/2011 | de Almeida et al. |

FOREIGN PATENT DOCUMENTS

| | | |
|---|---|---|
| WO | 02096881 A1 | 12/2002 |
| WO | 2004099153 A1 | 11/2004 |
| WO | 2005039497 A2 | 5/2005 |
| WO | 2006005951 A1 | 1/2006 |
| WO | 2006054115 A1 | 5/2006 |
| WO | 2006075925 A2 | 7/2006 |
| WO | 2006120501 A1 | 11/2006 |
| WO | 2007012793 A1 | 2/2007 |
| WO | 2007094694 A1 | 8/2007 |
| WO | 2007117166 A1 | 10/2007 |
| WO | 2008088233 A1 | 7/2008 |
| WO | 2009054743 A1 | 4/2009 |
| WO | 2011014084 A1 | 2/2011 |
| WO | 2011031176 A1 | 3/2011 |

OTHER PUBLICATIONS

Almeida et al., Neurotherapeutics, 2007;4(1): 88-96.*
WebMD (http://www.webmd.com/fibromyalgia/tc/fibromyalgia-prevention).*
Healthline (http://www.healthline.com/health/fibromyalgia-prevention).*
Ambrosio, Antonio F., et al., Mechanisms of Action of Carbamazepine and Its Derivatives, Oxcarbazepine, BIA 2-093, and BIA 2-024, XP009022844, Neurochemical Research, Feb. 2002, pp. 121-130, vol. 27, Nos. 1/2, Plenum Publishing Corporation.
Arnold, Lesley M., et al., Gabapentin in the Treatment of Fibromyalgia A Randomized, Double-Blind, Placebo-Controlled, Multicenter Trial, Arthritis & Rheumatism, Apr. 2007, pp. 1336-1344, vol. 56, No. 4, American College of Rheumatology.
Benes, Jan, et al., Anticonvulsant and Sodium Channel-Blocking Properties of Novel 10,11-Dihydro-5h-dibenz[b,f]azepine-5-carboxamide Derivatives, J. Med. Chem., 1999, pp. 2582-2587, vol. 42, American Chemical Society.
Bennet, R., The Fibromyalgia Impact Questionnaire (FIQ): a review of its developement, current version, operating characteristics and uses, Clin Exp Rheumatol, 2005, pp. S154-S162, vol. 23, Clinical and Experimental Rheumatology.
Burckhardt, Carol S., et al., The Fibromyalgia Impact Questionnaire: Development and Validation, 1991, vol. 18, No. 5, pp. 728-733, The Journal of Rheumatology.
Foriegn communication from a priority application—International Search Report and Written Opinion, PCT/PT2009/000043, Dec. 11, 2009, 8 pages.
Foreign communication from a priority application—International Preliminary Report on Patentability and Written Opinion, PCT/PT2009/000043, Jan. 31, 2012, 6 pages.
Hainzl, Dominik, et al., Metabolism of Two New Antiepileptic Drugs and Their Principal Metabolites S(+)- and R (−)-10,11-dihydro-10-hydroxy carbamazepine, Epilepsy Research, 2001, pp. 197-206, vol. 44, Elsevier Science B.V.
Hauser, Winfried, et al., Guidelines on the Management of Fibromyalgia Syndrome—A Systematic Review, European Journal of Pain, 2009, pp. 1-6, Elsevier Ltd.
Hays, Ron D., et al., Measuring Functioning and Well-Being The Medical Outcomes Study Approach, 1992, Chapter 14, pp. 235-259, plus cover page and publishing information, Duke University Press.
Mestre, Tiago, et al., Eslicarbazepine Acetate: A New Option for the Treatment of Focal Epilepsy, Expert Opin. Investig. Drugs, 2009, pp. 221-229, vol. 18, No. 2, Informa UK Ltd.
Montgomery, Stuart A., et al., A New Depression Scale Designed to be Sensitive to Change, Brit. J. Psychiat., 1979, pp. 382-389, vol. 134.
Pereira, Henrique, et al., Improvement in Quality-of-Life and Depressive Symptoms During Long-Term Treatment with Eslicarbazepine Acetate: BIA-2093-303 Study, Epilepsia, 2008, pp. 446-448, vol. 49, suppl. 7.
Wheeler-Aceto, Helen, et al., Standardization of the Rat Paw Formalin Test for the Evaluation of Analgesics, Psychopharmacology, 1991, pp. 35-44, vol. 104, Springer-Verlag.
Wolfe, Frederick, et al., The American College of Rheumatology 1990 Criteria for the Classification of Fibromyalgia, Arthritis and Rheumatism, Feb. 1990, pp. 160-172, vol. 33, No. 2.
Gennaro, Alfonso R.,et al., Remington: The Science and Practice of Pharmacy, 2000, cover page and publication information, vol. 1, 20th Edition, Lippincott Williams & Wilkins.
Geber, Christian, et al., Revised Definition of Neuropathic Pain and Its Grading System: An Open Case Series Illustrating Its Use in Clinical Practice, The American Journal of Medicine, Oct. 2009, pp. S3-S12, vol. 122, No. 10A, Elsevier Inc.
Briones-Vozmediano, Erica, et al., "Patients' and professionals' views on managing fibromyalgia," Pain Res Manag, 2013, vol. 18, No. 1, pp. 19-24.
Pubmed Health, "Carbamazepine for chronic neuropathic pain and fibromyalgia in adults," PubMed Health; National Library of Medicine, National Institutes of Health, 2014, http:/www.ncbi.nlm.nih.gov/pubmedhealth/PMH0013475/?report=printable, 2 pages.
Wiffen, Philip J., et al., "Antiepileptic drugs for neuropathic pain and fibromyalgia—an overview of Cochrane reviews," The Cochrane Collaboration, 2013, pp. 1-26 plus 2 cover pages, John Wiley & Sons, Ltd.
Späth et al., "Efficacy and safety of eslicarbazepine acetate as therapy in subjects with fibromyalgia: a double-blind, randomized, placebo-controlled, parallel-group, multicenter clinical trial," Clinical Study Report BIA-2093-210, v. 1.0, pp. 11-17 (2012), accessible through https://www.clinicaltrialsregister.eu/ctr-search/trial/2008-003557-32/results.

* cited by examiner

USE OF 5H-DIBENZ/B,F/AZEPINE-5-CARBOXAMIDE DERIVATIVES FOR TREATING FIBROMYALGIA

CROSS-REFERENCE TO RELATED APPLICATIONS

This application is a filing under 35 U.S.C. 371 of International Application No. PCT/PT2009/000043 filed Jul. 27, 2009, entitled "Use of 5H-Dibenz/b,f/Azepine-5-Carboxamide Derivatives for Treating Fibromyalgia," which application is incorporated by reference herein in their entirety.

FIELD OF THE INVENTION

This invention relates to the use of 5H-dibenz/b,f/azepine-5-carboxamide derivatives for treating fibromyalgia.

BACKGROUND

Fibromyalgia, also known as fibromyalgia/fibromyalgic syndrome (FMS), fibromyositis, polyinsertionitis, polyenthesopathy, myofibrositis, myofascitis, 'tension' rheumatism, 'psychogenic' muscular rheumatism, diffuse idiopathic pain syndrome (DIPS) or fibrositis, is a debilitating syndrome characterised by widespread chronic body pain and often with other symptoms such as fatigue, sleep disturbance, reduction in slow wave sleep, sensitivity to touch and light and cognitive problems. The National Fibromyalgia Association indicates that the syndrome affects ~3-6% of the world population. Current treatment includes pregabalin and it has been reported that gabapentin is effective in treating FMS symptoms (Arnold et al., (2007) *Arthritis Rheum.* 56(4):1336-44). The aetiology of the syndrome is still not yet fully understood and there is still an unmet need for an effective treatment with minimal side effects.

Eslicarbazepine acetate (ESL, S-(−)-10-acetoxy-10,11-dihydro-5H-dibenz/b,f/azepine-5-carboxamide; also known as BIA 2-093) is a new voltage-gated sodium channel (VGSC) blocker that shares with carbamazepine (CBZ) the dibenzazepine nucleus bearing the 5-carboxamide substituent, but is structurally different at the 10,11-position (see BENES, J., PARADA, A., FIGUEIREDO, A. A., ALVES, P. C., FREITAS, A. P., LEARMONTH, D. A., CUNHA, R. A., GARRETT, J. & SOARES-DA-SILVA, P, (1999), "Anticonvulsant and sodium channel-blocking properties of novel 10,11-dihydro-5H-dibenz[b,f]azepine-5-carboxamide derivatives," J Med Chem, 42, 2582-2587).

This molecular variation results in differences in metabolism, namely by preventing the formation of toxic epoxide metabolites, such as carbamazepine-10,11 epoxide, and unnecessary production of enantiomers or diastereoisomers of metabolites and conjugates (see HAINZL, D., PARADA, A. & SOARES-DA-SILVA, P. (2001), "Metabolism of two new antiepileptic drugs and their principal metabolites S(+)- and R(−)-10,11-dihydro-10-hydroxy carbamazepine," Epilepsy Res, 44, 197-206), without losing pharmacological activity (see the above Benes reference).

SUMMARY

According to a first aspect of the present invention, there is provided a 5H-dibenz/b,f/azepine-5-carboxamide derivative for the treatment of fibromyalgia.

According to a second aspect of the present invention, there is provided the use of a 5H-dibenz/b,f/azepine-5-carboxamide derivative in the manufacture of a medicament for the treatment of fibromyalgia.

According to a third aspect of the present invention, there is provided a method for the treatment of fibromyalgia, comprising administering a therapeutically effective amount of a 5H-dibenz/b,f/azepine-5-carboxamide derivative to a patient in need thereof.

In another aspect, the invention discloses a method of treating, preventing, or managing a disorder such as fibromyalgia comprising administering to a patient a therapeutically or prophylactically effective amount of a 5H-dibenz/b,f/azepine-5-carboxamide derivative such as eslicarbazepine acetate, or a pharmaceutically acceptable salt or solvate thereof. For example, the therapeutically or prophylactically effective amount of a 5H-dibenz/b,f/azepine-5-carboxamide derivative such as eslicarbazepine acetate, or a pharmaceutically acceptable salt or solvate thereof can be a daily dose in the range of about 200 mg to about 2400 mg, or in the range of about 400 mg to about 2400 mg, or in the range of about 650 mg to about 2000 mg, or in the range of about 750 mg to about 1500 mg, or in the range of about 600 mg to about 1600 mg.

DETAILED DESCRIPTION

As used herein, the term 'treatment' and variations such as 'treat' or 'treating' refer to the eradication or amelioration of a disease or disorder, or of one or more symptoms associated with the disease or disorder, in a human or non-human animal. In certain embodiments, the terms refer to minimizing the spread or worsening of the disease or disorder by the administration of one or more prophylactic or therapeutic agents to a subject with such a disease or disorder. The treatment may be in respect of the existing condition or may be prophylactic (preventative treatment). Treatment may include curative, alleviation or prophylactic effects. Treatment may prevent or delay the onset of, retard the progression of one or more of the symptoms of the FMS, or ameliorate one or more of the existing symptoms of FMS.

In some embodiments, the terms refer to the administration of a compound provided herein, with or without other additional active agent, after the onset of symptoms of the particular disease.

As used herein, and unless otherwise indicated, the terms "prevent," "preventing" and "prevention" refer to the prevention of the onset, recurrence or spread of a disease or disorder, or of one or more symptoms thereof. In certain embodiments, the terms refer to the treatment with or administration of a compound provided herein, with or without other additional active compound, prior to the onset of symptoms, particularly to patients at risk of disease or disorders provided herein. The terms encompass the inhibition or reduction of a symptom of the particular disease. Patients with familial history of a disease in particular are candidates for preventive regimens in certain embodiments. In addition, patients who have a history of recurring symptoms are also potential candidates for the prevention. In this regard, the term "prevention" may be interchangeably used with the term "prophylactic treatment."

As used herein, and unless otherwise specified, the terms "manage," "managing," and "management" refer to preventing or slowing the progression, spread or worsening of a disease or disorder, or of one or more symptoms thereof. Often, the beneficial effects that a subject derives from a prophylactic and/or therapeutic agent do not result in a cure of the disease or disorder. In this regard, the term "managing" encompasses treating a patient who had suffered from the particular disease in an attempt to prevent or minimize the recurrence of the disease.

As used herein, and unless otherwise specified, a "therapeutically effective amount" of a compound is an amount sufficient to provide a therapeutic benefit in the treatment or management of a disease or disorder, or to delay or minimize one or more symptoms associated with the disease or disorder. A therapeutically effective amount of a compound means an amount of therapeutic agent, alone or in combination with other therapies, which provides a therapeutic benefit in the treatment or management of the disease or disorder. The term "therapeutically effective amount" can encompass an amount that improves overall therapy, reduces or avoids symptoms or causes of disease or disorder, or enhances the therapeutic efficacy of another therapeutic agent.

As used herein, and unless otherwise specified, a "prophylactically effective amount" of a compound is an amount sufficient to prevent a disease or disorder, or prevent its recurrence. A prophylactically effective amount of a compound means an amount of therapeutic agent, alone or in combination with other agents, which provides a prophylactic benefit in the prevention of the disease. The term "prophylactically effective amount" can encompass an amount that improves overall prophylaxis or enhances the prophylactic efficacy of another prophylactic agent.

As used herein, and unless otherwise specified, the term "subject" is defined herein to include animals such as mammals, including, but not limited to, primates (e.g., humans), cows, sheep, goats, horses, dogs, cats, rabbits, rats, mice and the like. In specific embodiments, the subject is a human.

As used herein, and unless otherwise indicated, the term "pharmaceutically acceptable salt" refers to salts prepared from pharmaceutically acceptable non-toxic acids, including inorganic acids and organic acids. Suitable non-toxic acids include inorganic and organic acids such as, but not limited to, acetic, alginic, anthranilic, benzenesulfonic, benzoic, camphorsulfonic, citric, ethenesulfonic, formic, fumaric, furoic, gluconic, glutamic, glucorenic, galacturonic, glycidic, hydrobromic, hydrochloric, isethionic, lactic, maleic, malic, mandelic, methanesulfonic, mucic, nitric, pamoic, pantothenic, phenylacetic, propionic, phosphoric, salicylic, stearic, succinic, sulfanilic, sulfuric, tartaric acid, p-toluenesulfonic and the like.

As used herein, and unless otherwise indicated, the term "solvate" means a compound provided herein or a salt thereof, that further includes a stoichiometric or non-stoichiometric amount of solvent bound by non-covalent intermolecular forces. Where the solvent is water, the solvate is a hydrate.

The terms "fibromyalgia" and "fibrositis or fibromyositis or fibromyalgia syndrome" (FMS), as used interchangeably herein, describe several disorders, all characterized by achy pain and stiffness in soft tissues, including muscles, tendons, and ligaments. Various alternative terms for fibromyalgia disorders have been used in the past, including generalized fibromyalgia, primary fibromyalgia syndrome, secondary fibromyalgia syndrome, localized fibromyalgia, and myofascial pain syndrome.

In generalized fibromyalgia, which is about seven times more common in women than in men, the pain and stiffness are widespread, occurring throughout the body. Primary fibromyalgia syndrome is the most common variation of generalized fibromyalgia; it usually occurs in young or middle-aged women who have no associated or contributing underlying disorder.

Secondary fibromyalgia syndrome is a type of generalized fibromyalgia and refers to fibromyalgia symptoms in a person who has another underlying disorder that is causing the fibromyalgia symptoms, such as hypothyroidism. Other disorders, such as systemic lupus erythematosus or rheumatoid arthritis, may be associated with fibromyalgia, but may not be the underlying cause.

In localized fibromyalgia, pain and stiffness occur in a particular area, or at a few sites, such as the jaw, neck, and/or shoulder muscles. Localized fibromyalgia is somewhat more likely to occur in men, possibly because they are more likely to engage in more physically strenuous activities in occupational or sports situations. Sometimes, localized fibromyalgia gradually spreads to become generalized fibromyalgia. Myofascial pain syndrome is a type of localized or regional fibromyalgia which may occur in various sites. In the temporomandibular type, the chewing muscles on the side of the face are commonly involved and may become painful and tender.

Usually, the cause of generalized fibromyalgia is unknown; in primary fibromyalgia syndrome, the cause is always unknown. However, generalized fibromyalgia may be worsened by physical or mental stress, poor sleep, repetitive strains, an injury, or chronic exposure to dampness and cold. In secondary fibromyalgia syndrome, an underlying cause is known. The syndrome may occur as a complication of certain infections (for example, Lyme disease), or hypothyroidism. Another associated disorder, such as rheumatoid arthritis or systemic lupus erythematosus, may be coincidental or may sometimes increase the symptoms of fibromyalgia.

Localized fibromyalgia often results from an occupational or recreational muscle strain. The temporomandibular type of myofascial pain syndrome can be caused by clenching and grinding of the teeth, especially while the person is asleep.

Aching stiffness and pain usually develop gradually in generalized fibromyalgia. In localized fibromyalgia, however, the pain may begin suddenly after muscle strains, and be sharp. In both syndromes, the pain usually worsens with fatigue, straining, or overuse. Specific discrete areas of muscle may be tender when firm fingertip pressure is applied, these areas are called either tender or trigger points (both points are tender, but "trigger" points radiate the pain to a distant site). During flare-ups, muscle tightness or even spasms may occur. Any soft tissue (muscles, tendons, or ligaments) may be affected. Soft tissue of the neck, shoulders, chest and rib cage, lower back, and thighs as well as joints are especially likely to be painful.

In primary fibromyalgia syndrome, widespread pain typically occurs and is often accompanied by other symptoms, such as poor sleep, anxiety, depression, fatigue, and irritable bowel syndrome.

In the temporomandibular type of myofascial pain syndrome, the mouth often cannot be opened fully, and opening the mouth may be painful. Clenching or grinding of the teeth during sleep can lead to a headache on awakening that improves over the course of the day. Sometimes the teeth clenching or grinding continues throughout the day.

Symptoms of fibromyalgia include generalised pain such as diffuse, stabbing, shooting, aching, or throbbing pain, costochondritis, rachialgia of variable topography, cervicalgia, arthalgia, arnodalgia, dorsalgia or coccygodynia, dysmenorrhea, dyspareunia; numbness and/or tingling (paresthesia); burning; allodynia, e.g. mechanical allodynia; sensitivity to cold and/or heat, touch, and/or light; tender points sensitive to pressure; stiffness (especially in the morning); fatigue; sleep disturbance and disorders such as sleep apnea, sleep apnea syndrome, possibly accompanied by day-time somnolence, non-restorative sleep; digestive disorders such as irritable bowel syndrome, chronic colitis; headaches; migraine; abnormal motor activity such as restless leg syndrome, rachialgia, nocturnal myoclonus, sleep bruxis; abnormalities of dental articulations (e.g. SADAM syndrome); muscle weakness; urinary problems such as dysuria, urinary incontinence, urinary frequency, urinary urgency, cystalgia, urine leaks; skin complaints such as dry skin, rashes, tender skin, itchy skin; impaired coordination; impaired cognitive functions such as memory, concentration, vocabulary deficit, often significant and as if patient were 20 years older; dyspnea; dry eyes and/or mouth; rhinitis; nausea; affective and anxiety symptoms such as anxiety, depression; tinnitus; visual problems; vasomotor disorders such as acrocyanosis resembling Raynauld's syndrome, acroparesthesia, carpal tunnel syndrome, reticular livedo of inferior members, blood pressure instabilities; Raynaud's Syndrome; Sicca Syndrome (Siogren syndrome); oedema; weight gain; subjective swelling (i.e. reported by the patient but not detected by the observer); functional impotence.

According to a second aspect of the present invention, there is provided the use of a 5H-dibenz/b,f/azepine-5-carboxamide derivative in the manufacture of a medicament for the treatment of fibromyalgia.

According to a third aspect of the present invention, there is provided a method for the treatment of fibromyalgia, comprising administering a therapeutically effective amount of a 5H-dibenz/b,f/azepine-5-carboxamide derivative to a patient in need thereof.

Broadly, the 5H-dibenz/b,f/azepine-5-carboxamide derivatives used in the invention may be of the formula (I):

(I)

where $R_1$ is hydrogen, alkyl, halogenalkyl, aralkyl, cycloalkyl, cycloalkylalkyl, alkoxy, aryl, or pyridyl; the term alkyl means a straight or branched hydrocarbon chain containing from 1 to 18 carbon atoms; the term halogen means fluorine, chlorine, bromine or iodine; the term cycloalkyl means an alicyclic saturated group with 3 to 6 carbon atoms; and the term aryl means an unsubstituted phenyl group or phenyl substituted by alkoxy, halogen or nitro group.

The compounds of formula (I) are described in more detail in U.S. Pat. No. 5,753,646, the contents of which are incorporated herein by reference. The compounds may be prepared by acylating the 10,11-dihydro-10-hydroxy-5H-dibenz/b,f/azepine-5-carboxamide, as described in U.S. Pat. No. 5,753,646. More specifically, for example, to produce 10-acetoxy-10,11-dihydro-5H-dibenz/b,f/azepine-5-carboxamide it is possible to add acetylchloride in dichloromethane to a suspension of 10,11-dihydro-10-hydroxy-5H-dibenz/b,f/azepine-5-carboxamide and pyridine in dichloromethane, as described in example 4, of U.S. Pat. No. 5,753,646.

The compounds described in examples 4 to 17 of U.S. Pat. No. 5,753,646 can be produced by acylation using the appropriate acyl halide. The compounds described in examples 18 to 23 can be produced using the appropriate carboxylic acid.

The following compounds are examples of 5H-dibenz/b,f/azepine-5-carboxamide derivatives which may be used in the present invention:

(1) 10-acetoxy-10,11-dihydro-5H-dibenz/b,f/azepine-5-carboxamide;
(2) 10-benzoyloxy-10,11-dihydro-5H-dibenz/b,f/azepine-5-carboxamide;
(3) 10-(4-methoxybenzoyloxy)-10,11-dihydro-5H-dibenz/b,f/azepine-5-carboxamide;
(4) 10-(3-methoxybenzoyloxy)-10,11-dihydro-5H-dibenz/b,f/azepine-5-carboxamide;
(5) 10-(2-methoxybenzoloxy)-10,11-dihydro-5H-dibenz/b,f/azepine-5-carboxamide;
(6) 10-(4-nitrobenzoyloxy)-10,11-dihydro-5H-dibenz/b,f/azepine-5-carboxamide;
(7) 10-(3-nitrobenzoyloxy)-10,11-dihydro-5H-dibenz/b,f/azepine-5-carboxamide;
(8) 10-(2-nitrobenzoyloxy)-10,11-dihydro-5H-dibenz/b,f/azepine-5-carboxamide;
(9) 10-(4-chlorobenzoyloxy)-10,11-dihydro-5H-dibenz/b,f/azepine-5-carboxamide;
(10) 10-(3-chlorobenzoyloxy)-10,11-dihydro-5H-dibenz/b,f/azepine-5-carboxamide;
(11) 10-(2-acetoxybenzoyloxy)-10,11-dihydro-5H-dibenz/b,f/azepine-5-carboxamide;
(12) 10-propionyloxy-10,11-dihydro-5H-dibenz/b,f/azepine-5-carboxamide;
(13) 10-butyryloxy-10,1-dihydro-5H-dibenz/b,f/azepine-5-carboxamide;
(14) 10-pivaloyloxy-10,11-dihydro-5H-dibenz/b,f/azepine-5-carboxamide;
(15) 10-[(2-propyl)pentanoyloxy]-10,11-dihydro-5H-dibenz/b,f/azepine-5-carboxamide;
(16) 10-[(2-ethyl)hexanoyloxy]-10,11-dihydro-5H-dibenz/b,f/azepine-5-carboxamide;
(17) 10-stearoyloxy-10,11-dihydro-5H-dibenz/b,f/azepine-5-carboxamide;
(18) 10-cyclopentanoyloxy-10,11-dihydro-5H-dibenz/b,f/azepine-5-carboxamide;
(19) 10-cyclohexanoyloxy-10,11-dihydro-5H-dibenz/b,f/azepine-5-carboxamide;
(20) 10-phenylacetoxy-10,11-dihydro-5H-bibenz/b,f/azepine-5-carboxamide;
(21) 10-(4-methoxyphenyl)acetoxy-10,11-dihydro-5H-dibenz/b,f/-azepine-5-carboxamide;

(22) 10-(3-methoxyphenyl)acetoxy-10,11-dihydro-5H-dibenz/b,f/azepine-5-carboxamide;
(23) 10-(4-nitrophenyl)acetoxy-10,11-dihydro-5H-dibenz/b,f/azepine-5-carboxamide;
(24) 10-(3-nitrophenyl)acetoxy-10,11-dihydro-5H-dibenz/b,f/azepine-5-carboxamide;
(25) 10-nicotinoyloxy-10,11-dihydro-5H-dibenz/b,f/azepine-5-carboxamide;
(26) 10-isonicotinoyloxy-10,11-dihydro-5H-dibenz/b,f/azepine-5-carboxamide;
(27) 10-(4-aminobutanoyloxy)-10,11-dihydro-5H-dibenz/b,f/azepine-5-carboxamide;
(28) 10-(2-amino-3-methylbutanoyloxy)-10,11-dihydro-5H-dibenz/b,f/-azepine-5-carboxamide;
(29) 10-chloroacetoxy-10,11-dihydro-5H-dibenz/b,f/azepine-5-carboxamide;
(30) 10-bromoacetoxy-10,11-dihydro-5H-dibenz/b,f/azepine-5-carboxamide;
(31) 10-formyloxy-10,11-dihydro-5H-dibenz/b,f/azepine-5-carboxamide;
(32) 10-ethoxycarbonyloxy-10,11-dihydro-5H-dibenz/b,f/azepine-5-carboxamide;
(33) 10-(2-chloropropionyloxy)-10,11-dihydro-5H-dibenz/b,f/azepine-5-carboxamide.

The 10,11-dihydro-10-hydroxy-5H-dibenz/b,f/azepine-5-carboxamides may be resolved into their (R)-(+)- and (S)-(−)-stereoisomers, whereby the desired (R)-(+)- or (S)-(−)-stereoisomer of the above compounds may be produced. Alternatively, a mixture of the stereoisomers may be used, in particular, the racemate.

The 5H-dibenz/b,f/azepine-5-carboxamide derivatives used in the invention may also be manufactured using processes described in WO02/092572 and WO02/096881.

Advantageously, the 5H-dibenz/b,f/azepine-5-carboxamide derivative is selected from eslicarbazepine acetate; R-licarbazepine acetate; or a mixture of eslicarbazepine acetate and R-licarbazepine acetate, for example the racemate.

In another embodiment, the 5H-dibenz/b,f/azepine-5-carboxamide derivative is selected from eslicarbazepine; R-licarbazepine; or a mixture of eslicarbazepine and R-licarbazepine, for example the racemate.

In still another embodiment, the 5H-dibenz/b,f/azepine-5-carboxamide derivative is oxcarbazepine (10,11-dihydro-10-oxo-5H-dibenz/b,f/azepine-5-carboxamide).

The 5H-dibenz/b,f/azepine-5-carboxamide derivatives used in the invention may be formulated into pharmaceutical compositions useful for treating fibromyalgia. Such compositions comprise the 5H-dibenz/b,f/azepine-5-carboxamide derivative, such as eslicarbazepine acetate; R-licarbazepine acetate; or a mixture thereof, in combination with a pharmaceutically acceptable carrier, adjuvant, vehicle or excipient. The 5H-dibenz/b,f/azepine-5-carboxamide derivatives can be administered alone or in combination with one or more other active pharmaceutical ingredients such as analgesics, antidepressants. Non-limiting examples of antidepressants include, without limitation, selective serotonin reuptake inhibitors, serotonin reuptake inhibitors, norepinephrine reuptake inhibitors, serotonin norepinephrine reuptake inhibitor (SNRI) e.g. milnacipran, minalcipran, and dopamine reuptake inhibitors. The term "analgesic" refers to any member of the diverse group of drugs used to relieve pain. Analgesic drugs act in various ways on the peripheral and central nervous systems. They include, but are not limited to, paracetamol (acetaminophen), the nonsteroidal anti-inflammatory drugs (NSAIDs), and opiate drugs such as morphine. In such cases, the 5H-dibenz/b,f/azepine-5-carboxamide derivatives may be administered simultaneously, for example in a single dosage form, or sequentially.

The present invention discloses a method of treating, preventing, or managing fibromyalgia comprising co-administrating a therapeutically or prophylactically effective amount of a 5H-dibenz/b,f/azepine-5-carboxamide derivate, such as, for example, eslicarbazepine acetate, and one or more analgesic or antidepressant. This type of combination therapy is advantageous because the co-administration of active ingredients achieves a therapeutic effect that is greater than the therapeutic effect achieved by administration of only a single therapeutic agent. In one embodiment, the co-administration of two or more therapeutic agents achieves a synergistic effect, i.e., a therapeutic effect that is greater than the sum of the therapeutic effects of the individual components of the combination. In another embodiment, the co-administration of two or more therapeutic agents achieves an augmentation effect. The active ingredients that comprise a combination therapy can be administered together via a single dosage form or by separate administration of each active agent. In certain embodiments, the first and second therapeutic agents are administered in a single dosage form. The agents can be formulated into a single tablet, pill, or capsule, and the like. Alternatively, the first therapeutic agent and the second therapeutic agents can be administered as separate compositions, e.g., as separate tablets or solutions. The first active agent can be administered at the same time as the second active agent or the first active agent can be administered intermittently with the second active agent. The length of time between administration of the first and second therapeutic agent can be adjusted to achieve the desired therapeutic effect. In certain instances, the second therapeutic agent can be administered only a few minutes (e.g., 1, 2, 5, 10, 30, or 60 min) after administration of the first therapeutic agent. Alternatively, the second therapeutic agent can be administered several hours (e.g., 2, 4, 6, 10, 12, 24, or 36 hr) after administration of the first therapeutic agent. In certain embodiments, it can be advantageous to administer more than one dosage of the second therapeutic agent between administrations of the first therapeutic agent. For example, the second therapeutic agent can be administered at 2 hours and then again at 10 hours following administration of the first therapeutic agent. Alternatively, it can be advantageous to administer more than one dosage of the first therapeutic agent between administrations of the second therapeutic agent. Importantly, it is preferred that the therapeutic effects of each active ingredient overlap for at least a portion of the duration of each therapeutic agent so that the overall therapeutic effect of the combination therapy is attributable in part to the combined or synergistic effects of the combination therapy.

Pharmaceutically acceptable carriers, adjuvants, excipients and vehicles that may be used in the pharmaceutical compositions of this invention are those conventionally employed in the field of pharmaceutical formulation, and include, but are not limited to, sugars, sugar alcohols, starches, ion exchangers, alumina, aluminium stearate, lecithin, serum proteins, such as human serum albumin, buffer substances such as phosphates, glycerine, sorbic acid, potassium sorbate, partial glyceride mixtures of saturated vegetable fatty acids, water, salts or electrolytes, such as protamine sulphate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The pharmaceutical compositions of this invention may be administered orally, by inhalation spray, rectally, nasally, buccally, vaginally or via an implanted reservoir. Oral administration is preferred. The pharmaceutical compositions of this invention may contain any conventional non-toxic pharmaceutically-acceptable carriers, adjuvants or vehicles.

The pharmaceutical compositions of this invention may be orally administered in any orally acceptable dosage form including, but not limited to, capsules, tablets, powders, granules, and aqueous suspensions and solutions. These dosage forms are prepared according to techniques well-known in the art of pharmaceutical formulation. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are administered orally, the active ingredient is combined with emulsifying and suspending agents.

The compounds of the invention can be administered to a patient in a daily dosage (such as once-daily) amount of between 20 mg to 2400 mg, including 20 mg to 1200 mg and 400 mg to 1200 mg, for example 400 mg, 600 mg, 800 mg, 1200 mg, 1800 mg and 2400 mg of active ingredient.

The amount to be administered to a subject (e.g., patient) to treat, prevent, and/or manage the disorders described herein will depend upon a variety of factors including the activity of the particular compound employed, the route of administration, the time of administration, the rate of excretion or metabolism of the particular compound being employed, the duration of the treatment, other drugs, compounds and/or materials used in combination with the particular compound employed, the age, sex, weight, condition, general health, and prior medical history of the patient being treated, and like factors well known in the medical arts.

A physician or veterinarian having ordinary skill in the art can readily determine and prescribe the effective amount required. For example, the physician or veterinarian could start doses of the compounds employed at levels lower than that required in order to achieve the desired therapeutic effect and gradually increase the dosage until the desired effect is achieved.

In general, a suitable daily dose of a compound provided herein will be that amount of the compound which is the lowest dose effective to produce a therapeutic or prophylactic effect. Such an effective dose will generally depend upon the factors described above. Generally, oral, intravenous, intracerebroventricular and subcutaneous doses of the compounds provided herein for a patient will range from about 0.005 mg per kilogram to about 5 mg per kilogram of body weight per day. In one embodiment, the oral dose of a compound provided herein will range from about 20 mg to about 3 g per day. For example, daily dosage of the active ingredient can be 20 mg/day, 100 mg/day, 200 mg/day, 400 mg/day, 500 mg/day, 650 mg/day, 700 mg/day, 750 mg/day, 800 mg/day, 850 mg/day, 900 mg/day, 950 mg/day, 1000 mg/day, 1050 mg/day, 1100 mg/day, 1150 mg/day 1,200 mg/day, 1250 mg/day, 1300 mg/day, 1350 mg/day, 1400 mg/day, 1450 mg/day, 1500 mg/day, 1600 mg/day, 1700 mg/day, 1800 mg/day, 1900 mg/day, 2000 mg/day, 2100 mg/day, 2200 mg/day, 2300 mg/day, 2400 mg/day. In one embodiment, the oral dose of a compound provided herein will range from about 200 mg to about 2.4 g per day. In one embodiment, the oral dose of a compound provided herein will range from about 500 mg to about 2.4 g per day. In one embodiment, the oral dose of a compound provided herein will range from about 550 mg to about 2000 mg per day. In another embodiment, the oral dose of a compound provided herein will range from about 650 mg to about 1600 mg per day. In another embodiment, the oral dose of a compound provided herein will range from about 750 mg to about 1500 mg per day. In one embodiment, the oral dose of a compound provided herein will range from about 750 mg to about 2400 mg per day. In another embodiment, the oral dose of a compound provided herein will range from about 750 mg to about 2000 mg per day. In another embodiment, the oral dose of a compound provided herein will range from about 500 mg to about 1200 mg per day. In another embodiment, the oral dose of a compound provided herein will range from about 550 mg to about 1300 mg per day. Each of the above-recited dosage ranges may be formulated as a single or multiple unit dosage formulations. Unit dosages of the active ingredient can be formulated as, for example, 50 mg, 100 mg, 200 mg, 400 mg, 500 mg, 550 mg, 600 mg, 650 mg, 700 mg, 750 mg, 800 mg, 850 mg, 900 mg, 950 mg, 1000 mg, 1050 mg, 1100 mg, 1150 mg, 1200 mg, 1300 mg, 1400 mg, 1500 mg, 1600 mg, 1700 mg, 1800 mg, 1900 mg, 2000 mg, or 2400 mg.

In one embodiment, the compounds described herein treat, prevent, and/or manage fibromyalgia, without causing addiction to said compounds.

Pharmaceutical compositions provided herein that are suitable for oral administration can be presented as discrete dosage forms, such as, tablets (e.g., chewable tablets), caplets, capsules, and liquids. Such dosage forms contain predetermined amounts of active ingredients, and may be prepared by methods of pharmacy well known to those skilled in the art. See generally, *Remington: The Science and Practice of Pharmacy*, 20$^{th}$ Ed. (2000).

Because of their ease of administration, tablets and capsules represent the most advantageous oral dosage unit forms, in which case solid excipients are employed. Such dosage forms can be prepared by any of the methods of pharmacy. In general, pharmaceutical compositions and dosage forms are prepared by uniformly and intimately admixing the active ingredients with liquid carriers, finely divided solid carriers, or both, and then shaping the product into the desired presentation if necessary.

Suitable formulations for use in the invention are described in WO2009/054743, incorporated herein in its entirety by reference thereto.

Kits

In some cases, active ingredients used in methods and compositions provided herein are preferably not administered to a patient at the same time or by the same route of administration. Therefore, provided are kits which, when used by the medical practitioner, can simplify the administration of appropriate amounts of active ingredients to a patient.

In one embodiment, the kit comprises a single unit dosage form of the compounds and composition provided herein, or a pharmaceutically acceptable salt, solvate, or stereoisomer thereof, and a single unit dosage form of another agent that may be used in combination with those compounds. Kits provided herein can further comprise devices that are used to administer the active ingredients. Examples of such devices include, but are not limited to, syringes, drip bags, patches, and inhalers.

Kits provided herein can further comprise pharmaceutically acceptable vehicles that can be used to administer one or more active ingredients.

Certain embodiments are exemplified in the following non-limiting examples. It will be apparent to those skilled in the art that many modifications, both to materials and methods, can be practised without departing from the spirit and scope of this disclosure.

The compounds of the invention were evaluated in the following studies. Animal models were used to evaluate efficacy in humans according to acceptable models for usefulness in humans. The examples demonstrate that the compounds of the present invention are capable of impacting multiple facets of fibromyalgia, and are capable of treating, preventing, and/or managing fibromyalgia.

Study 1—Paw Withdrawal in CCI Mice

1. Objectives:

The objectives of the study were:

1.1 To assess the potential analgesic effects of ESL using an established behavioural test (von Frey filaments) in mice with chronic constriction nerve injury (CCI).

1.2 To compare the effects of ESL with those of the drug vehicle and gabapentin, a compound known to be effective in inhibiting mechanical allodynia induced by peripheral nerve injury.

Figure 1:
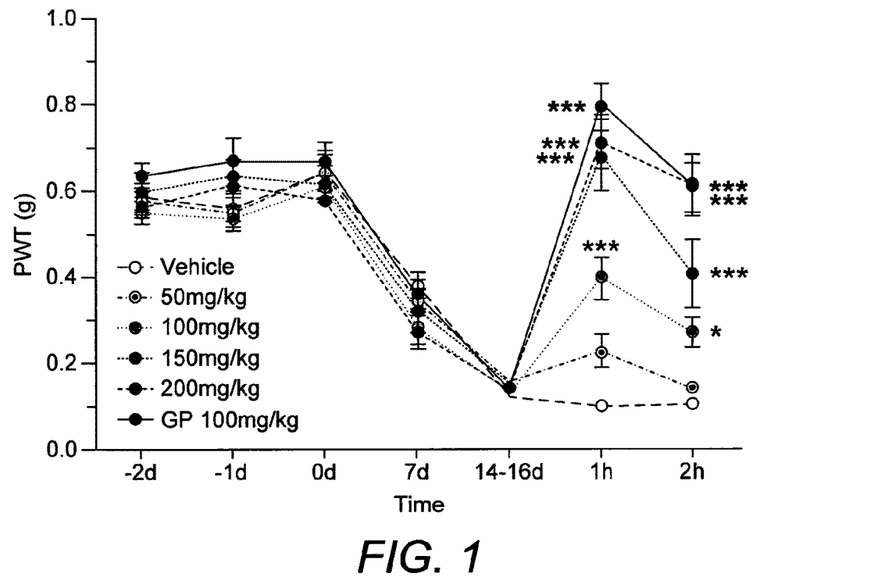
FIG. 1 shows the dose-response relationship of ESL on PWT in ipsilateral limbs of CCI mice.
Figure 2:
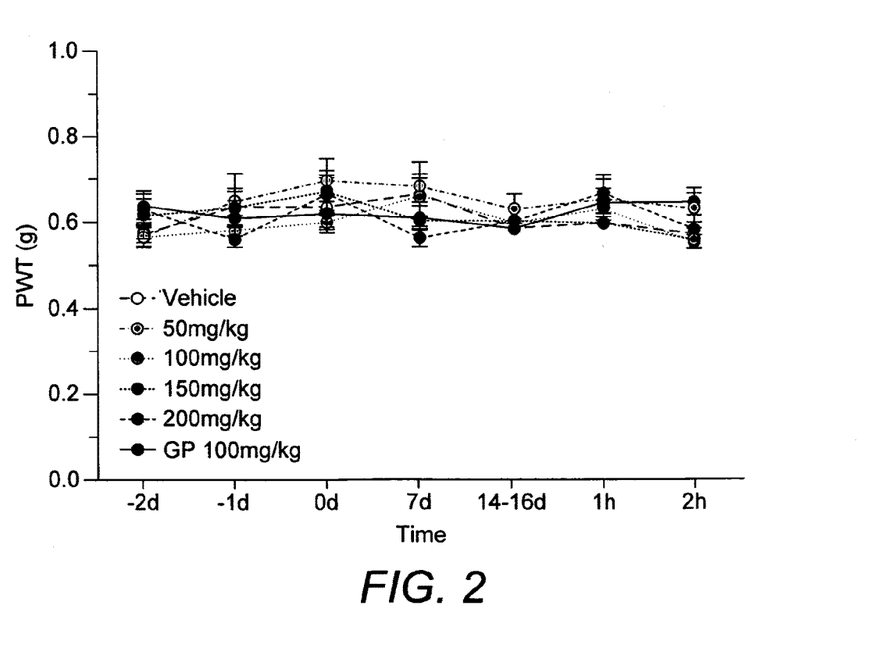
FIG. 2 shows the effects of the vehicle, gabapentin and ESL at different doses on PWT in the contralateral limbs of CCI mice.

2. Materials and Methods:

The materials used were (as also indicated in FIGS. 1 and 2):

Vehicle: 0.5% hydroxy-propyl-methyl-cellulose (HPMC) in water, 5 ml/kg, p.o.;

50 mg/kg, 100 mg/kg, 150 mg/kg and 200 mg/kg: ESL at 50, 100, 150 and 200 mg/kg, p.o.;

GP 100 mg/kg: gabapentin 100 mg/kg, p.o.

The potential analgesic effects of orally dosed ESL was investigated at doses of 50, 100, 150 and 200 mg/kg, on the paw withdrawal threshold (PWT) and these effects compared with those of the dose vehicle and gabapentin, the latter at 100 mg/kg, in a mouse model of chronic constriction nerve injury (CCI).

Each animal received a single oral dose of either ESL (50, 100, 150, or 200 mg/kg), or gabapentin (100 mg/kg in saline) or vehicle (5 ml/kg). Behavioural testing was then performed twice, at approximately 60 and 120 minutes post-dose, to investigate the effect of treatments.

3. Results:

The results of the experiments are shown in FIGS. 1 and 2, in which:

FIG. 1 shows the dose-response relationship of ESL on PWT in ipsilateral limbs of CCI mice.

*, , *, indicate P<0.05, 0.01 and 0.001 compared to the same time points as vehicle group (One-way ANOVA).

FIG. 2 shows the effects of the vehicle, gabapentin and ESL at different doses on PWT in the contralateral limbs of CCI mice. No significant difference was found for all time points compared with the vehicle treated group (P>0.05 for all time points, One-Way ANOVA) except for the 50 mg/kg group on 14th to 16th day and the gabapentin treated group at 2 hour after dosing, where the PWT was significantly higher than that observed in the vehicle group (P<0.05).

In the CCI model mice, the vehicle did not significantly affect the PWT. ESL, dosed orally, dose-dependently increased the PWT in the ipsilateral hindpaw. The effect lasted for more than 2 hours after dosing. Gabapentin, employed as a positive control, at 100 mg/kg, also significantly increased PWT.

Plasma bioanalysis showed that ESL was completely metabolized within 1 hour after administration and mainly to eslicarbazepine. The plasma concentrations of eslicarbazepine were positively correlated with the doses of ESL administered.

These results led to the following conclusions:

1. The test drug vehicle did not affect PWT in CCI model mice.

2. Gabapentin, at 100 mg/kg, p.o., produced a significant increase in PWT in CCI model mice.

3. ESL dose-dependently increased PWT in the ipsilateral limbs in CCI model mice and did not significantly affect the PWT in the contralateral side, indicating a selective efficacy.

ESL displayed potency and efficacy similar to the reference compound, gabapentin. These data indicate that ESL has an anti-allodynic action in the chronic constriction nerve injury model of neuropathic pain in mice and a therapeutic effect on the neuropathic state induced by chronic constriction nerve injury.

Therefore, ESL would be useful in the treatment of fibromyalgia in humans, for example in a once-daily administration, and in daily dosage amounts of between 20 mg to 2400 mg/day, for example 400 mg, 600 mg, 800 mg or 1,200 mg/day. Unit dosages may be formulated as 200 mg, 400 mg, 600 mg, 800 mg or 1200 mg.

Study 2—Ectopic Discharge of Peripheral Nerve Filaments and Spontaneous Activity of Dorsal Horn Neurones 1. Objectives The effects of ESL on ectopic discharge of peripheral nerve filaments and spontaneous activity of dorsal horn neurones were investigated in mice with chronic constriction injury (CCI). The study was divided into 2 parts:

Part 1

A series of peripheral nerve recording configurations were used to determine the ectopic discharge generated at the level of the neuroma, dorsal root ganglion (DRG) or both.

Part 2

A series of surgical procedures, including spinalisation and dorsal root sectioning, were employed to investigate the site(s) of action of ESL.

The objectives were:

1. To examine the effects of ESL on ectopic discharge in peripheral nerves of CCI mice.
2. To examine the site(s) of action of ESL in CCI mice using a series of peripheral nerve preparations in vivo.
3. To examine the effects of ESL on spontaneous activity of dorsal horn neurones in CCI mice.
4. To examine the site(s) of action of ESL in CCI mice using a series of experimental preparations (dorsal root sectioning and spinalisation) in vivo.

2. Materials and Methods

Adult male BL CB F1 mice, weighing 25-30 g at the time of surgery and 26-38 g at the time of electrophysiological experiments, were used. The baseline paw withdrawal threshold (PWT) was examined using a series of graduated von Frey hairs (see below) on 3 consecutive days before surgery and re-assessed on the $7^{th}$ and on the $14^{th}$ days after surgery, before electrophysiological recording. The animals were killed by an overdose of pentobarbitone on completion of the study.

2.2. Surgery

The chronic constriction injury (CCI) model was prepared following the standard protocols described previously (Bennett and Xie, 1988). Mice were anaesthetised and the lateral side of the left thigh was shaved and sterilized with 75% ethanol. A small incision of approximately 0.5 cm was made parallel to the femur. The muscle was carefully separated to expose the sciatic nerve. Three loose ligatures were placed on the sciatic nerve with 5-0 suture silk thread at approximately 1 mm intervals. The wound was closed in layers with suture silk 4-0 and the animals were placed in a recovery chamber with the temperature controlled and set at 30° C. A dose of amoxicillin (0.02 mL, 3 mg) was routinely injected i.p. after surgery to prevent infection. The animals were returned to their home cages after complete recovery of consciousness and freedom of movement. For the first 2 days after surgery, the animals were closely monitored at least twice daily and subsequently, at least once daily until compound testing.

2.3. Assessment of Mechanical Allodynia

Each animal was placed in a perspex cage on a metal mesh. A series of von Frey filaments (0.07 g, 0.16 g, 0.4 g, 0.6 g, 1.0 g) were applied to the plantar surface of the hind-paw, from below. The filaments were applied in ascending order (starting with the lowest force 0.07 g) to both ipsilateral and contralateral hind-paws. Each filament was applied 10 times with a protocol of one second on, one second off. The PWT was defined as being the lowest force required to elicit at least 5 paw withdrawal responses out of 10 trials.

The baseline PWT was tested for 3 consecutive days before surgery and re-assessed on the $7^{th}$ and $14^{th}$ days after surgery to monitor the development of mechanical allodynia. Only those mice showing significant mechanical allodynia (PWT≤0.2 g) were selected for subsequent electrophysiological experiments.

2.4. Electrophysiological Recording

Part 1

The mice were re-anaesthetised and the sciatic nerve was exposed via a dorsal incision on the hind-limb. The skin was secured (stitched) to a metal O-ring to form an oil pool for recording nerve activity. A reference electrode was connected to the metal O-ring to form a closed circuit with the nerve recording electrode. To record ectopic discharge generated from the intact animal, under a microscope, the small bundles of sural nerve (distal to the ligated area) were repeatedly teased and looped onto a unipolar silver electrode for examination. To facilitate the recording of ectopic discharge generated from the neuroma (ligated area) or from the DRG, the sciatic nerve was separated carefully from the surrounding connective tissues, sectioned at a more proximal site leaving the injured area intact or near the injured area leaving the more proximal part intact. A small bundle of nerve filaments were teased from the sciatic nerve from either the distal or proximal cut end of the sciatic nerve, to record neuroma-generated ectopic discharge, or from the proximal cut end to record DRG-generated ectopic discharge. The filament was looped on to a unipolar silver wire recording electrode with an indifference electrode connected to the connective tissues nearby, allowing the spontaneous activity generated from either the ligated area (sensitized axons) or from DRG (somata) to be recorded. The electrical signals were then recorded through a CED micro-1401 interface to a PC for later off-line analysis. Recording from a fibre with spontaneous activity was undertaken for at least 10 min for control and 40 min after either vehicle or ESL administration.

Part 2

After behavioural validation, the mice were re-anaesthetised, body temperature was monitored and controlled within a physiological range via a thermo-blanket system, and the electrocardiogram (ECG) was routinely monitored through a pair of stainless steel needles inserted into the left fore-paw and right hind-paw.

A laminectomy was carried out to expose the L2-L6 segments of the spinal cord. In some experiments, spinalisation at the C2-C3 level or section of the L4-L6 dorsal roots of the left side at a site near the root entry zone to the spinal cord, was performed. A protective pool was formed and filled with warm mineral oil to cover the spinal cord and the sectioned roots. Extracellular unitary recordings of spontaneous activity from the spinal dorsal horn neurones were achieved by using a carbon microelectrode driven by an electrode manipulator. The electrical signals were recorded through a CED micro-1401 interface to a PC for later off-line analysis. Recording from a dorsal horn neurone displaying spontaneous electrical discharge was undertaken for a period of at least 10 min for control and 40 min after either vehicle or ESL administration.

2.5. Drug Administration

The suspension was prepared with a vehicle containing 30% DMSO in 0.9% sodium chloride to a dose concentration of 50 mg/mL. The vehicle and ESL were injected intraperitoneally at a volume of 2 mL/kg through a needle connected with a 1 mL syringe placed prior to the experiment. Each animal received only one treatment of either vehicle or ESL (100 mg/kg).

2.6. Data Processing

Spontaneous activity was counted as firing rate per minute. An average firing rate over 5 min periods, recorded consecutively immediately prior to vehicle injection or ESL was used as control (and standardized as 100%). The average firing rate over a 5 min period recorded 30-35 min after vehicle or ESL injection was used to quantify firing rate following treatment and compared with the control level. Due to the high level of variation in frequency of spontaneous ectopic discharge from preparation to preparation; all data were standardized relative to control. All data were expressed as mean±SEM. A paired Student's t-test (two-way) was used to compare different time points in the same group. The significance level was set at P<0.05. Unpaired Student's t-test, assuming equal or unequal as where appropriate, was employed to compare the results of different treatments (e.g., vehicle versus ESL).

3. Results

Part 1

Effects of Vehicle and ESL on Ectopic Discharge in Intact CCI Mice

In 5 preparations, spontaneous ectopic discharge varied between 355.4 and 2927.0 impulses/min (mean±SEM: 1607.3±413.7 imps/min). In 3 out of 5 preparations, vehicle induced a slight inhibition of ectopic discharge, from 100% to between 89.0% and 90.7% of control level, 30 min after injection. In one preparation, the firing rate increased to 110.3% of control level 30 min after vehicle injection. In the remaining preparation the firing rate did not significantly change (99.5% of control level). Overall, ectopic discharge after vehicle injection was 96.0±4.0% of control (1511.5±366.9 imps/min). Whether expressed as absolute spike numbers or normalised as a percentage of control, ectopic discharge following administration of vehicle was not significantly different from control levels (P>0.05, paired Student's t-test).

In contrast, in a separate group of 5 preparations, ESL, at 100 mg/kg, ip, induced a significant inhibition of ectopic discharge to 699.8±339.7 imps/min (26.6±10.6% of control level) from a control value of 2048.0±391.6 imps/min (P<0.001, compared to control, paired Student's t-test; and P<0.01, compared to the vehicle group, Student's t-test for two samples assuming unequal variance).

Effects of Vehicle and ESL on Ectopic Discharge of Neuroma-Origin in CCL Mice

In 5 preparations with the sciatic nerve sectioned at the proximal end, similar observations were made to those recorded in the 'intact' preparations. Thus, vehicle did not induce any significant change in ectopic discharge. The average firing rate of ectopic discharge ranged between 108.0 to 1940.8 imps/min (894.5±302.1 imps/min), before vehicle injection. 30 min after vehicle injection, in general, the firing rate of ectopic discharge was not significantly changed (897.5±218.0 imps/min), although in two preparations, the firing rate increased from 108 to 217 imps/min in one preparation and from 575.4 to 865.8 imps/min in another preparation.

Sectioning of the sciatic nerve proximal to the nerve injured area (neuroma preparation) did not significantly change the effects of ESL in inhibiting ectopic discharge in CCI mice. In five preparations, ESL significantly inhibited ectopic discharge from 1390.6±378.5 imps/min in control to 643.5±249.2 imps/min, 30 min after injection of ESL. This amounted to a reduction in ectopic discharge to 36.5±12.3% of control levels (P<0.01, compared to pre-dosing level in percentage, paired Student's t-test). ESL induced inhibition of ectopic discharge of neuroma origin was not significantly different from that observed in intact animals (P>0.05, Student's t-test for two samples assuming unequal variance).

Effects of Vehicle and ESL on Ectopic Discharge of DRG-Origin in CCI Mice

To examine if ESL inhibits ectopic discharge of DRG-origin, in 11 CCI mice, a section of the sciatic nerve was undertaken just above the ligated area to facilitate the recording of spontaneous activity generated at the level of the DRG. In 5 preparations, the effect of vehicle was examined. Generally, the vehicle did not significantly affect ectopic discharge of DRG-origin. In 3 out of 5 preparations, the spontaneous ectopic discharge was reduced from 383.4, 180.0 and 429.4 imps/min in control to 296.4, 174.2 and 345.4 imps/min, respectively at 30 min following vehicle injection. In the other 2 preparations, the firing rates were slightly increased from 347.4 and 288.4 imps/min in control to 403.6 and 329.6 imps/min, respectively following vehicle injection. The average firing rate was 325.7±43.1 imp/min before vehicle and 309.8±38.1 imps/min after vehicle injection, ectopic discharge following vehicle injection amounting to 97.0±8.2% of control level (P>0.05, paired student's t-test).

In contrast, in all 6 preparations tested, ESL, following i.p. injection at 100 mg/kg, produced a significant reduction in ectopic discharge. The average firing rate was reduced from 514.3±141.0 imps/min in control to 274.4±117.1 imps/min following injection of ESL. This amounted to a reduction in ectopic discharge to 58.43±13.21% of control in the presence of BIA-2-194 (P<0.05 compared to the vehicle control, Student's t-test assuming for two samples assuming unequal variance).

There was no significant difference in the effects of ESL between the different recording configurations tested (P>0.05, Student's t-test for two samples assuming equal variance). However, there was a tendency for ESL to be less effective on ectopic discharge of DRG-origin.

Part 2

Effects of Vehicle and ESL on Spontaneous Activity in Intact CCI Mice

In 7 preparations, spontaneous discharge of dorsal horn neurones varied between 76.8 and 869.0 impulses/min, with an average value of 413.8±115.07 imps/min (mean±SEM) prior to vehicle injection. At 30-35 min after injection, spontaneous activity ranged between 127.6 and 2748 imps/min with an average value of 683.6±347.3 imps/min. In 2 out of 7 preparations, vehicle induced an inhibition of spontaneous discharge, from 100% to 59.4% and 73.9% of control levels, respectively. In 3 preparations, the firing rate increased to between 101.2 and 166.0% of control level after vehicle injection. In the remaining 2 preparations the firing rate increased greatly to 342.4% and 389.2%, respectively, after vehicle injection. Overall, the average spontaneous discharge at 30-35 min after vehicle injection was 177.9±50.4% of control. Whether calculated in spike number or expressed as a percentage of control, spontaneous activity following administration of vehicle was not significantly different from the control level (P>0.05, paired Student's t-test).

In contrast, in a separate group of 5 preparations, ESL, at 100 mg/kg, i.p., induced a significant inhibition of spontaneous activity. ESL, at 100 mg/kg, i.p., induced a significant inhibition of spontaneous activity from a control value of 780.7±462.5 imps/min to 113.6±43.9 imps/min (26.3±10.1% of control level) at 30-35 min following injection of the drug (P<0.01, compared to control; paired Student's t-test; and P<0.05, compared to the vehicle group; Student's t-test for two samples assuming unequal variance).

Effects of Vehicle and ESL on Spontaneous Activity of Dorsal Hornneurones in Pinalised CCI Mice To exclude the possibility that the effects of ESL in inhibiting spontaneous activity of dorsal horn neurones were due to the activation of descending inhibitory pathways, surgical spinalisation at the C2-C3 level was employed in 10 CCI mice. In 5 mice, 30-35 min after vehicle administration, spontaneous activity slightly but significantly increased (expressed as a percentage of control, P<0.05, paired Student's t-test). The average firing rate of spontaneous activity increased from 297.3±59.7 imps/min (ranged between 179.8 imps/min and 477.8 imps/min) before vehicle injection to 454.1±74.4 imps/min (ranged between 282.0 and 689.6 imps/min; P>0.05 compared with control). Although in one preparation, the firing rate decreased slightly, from 477.8 to 457.0 imps/min, in the remaining four preparations firing rate increased from 252.2±50.5 to 453.4±96.1 imps/min following injection of vehicle.

The inhibitory effects of ESL on spontaneous activity in CCI mice persisted following spinalisation at the C2-C3 level. ESL, in 5 preparations, induced inhibition of spontaneous activity from 504.5±286.1 imps/min in control to 31.2±12.7 imps/min at 30-35 min after injection of the drug. However, due to the considerable variation in spontaneous firing rate from preparation to preparation, the inhibitory effect of ESL did not reach statistical significance (P>0.05). Thus data were normalised and expressed as a percentage of control. ESL significantly reduced spontaneous activity in these spinalised preparations to 14.8±6.8% of control levels (P<0.001, compared to pre-dosing level expressed as a percentage, paired Student's t-test). Average firing rate expressed as either spike number or percentage was significantly lower compared to the vehicle group (P<0.001, unpaired student's t-test). The BIA 2 194 induced inhibition of spontaneous activity after spinalisation was not significantly different from that observed in the intact animals (P>0.05, Student's t-test for two samples assuming unequal variance).

Effects of Vehicle and ESL on Spontaneous Activity of Dorsal Horn Neuronesin CCI Mice with Dorsal Root Sectioned To examine whether the effects of ESL on spontaneous activity of dorsal horn neurones were due to the inhibition of spontaneous activity of peripheral nerves (e.g. reducing the sensory inputs originating from DRG and neuroma), a section of the dorsal root at L4-L6 was undertaken in 14 CCI mice. In 6 preparations, the effect of vehicle was examined. In two out of six preparations, the spontaneous activity was reduced from 869.0 and 759.4 imps/min in control to 279.4 and 602.6 imps/min, respectively at 30-35 min following vehicle injection. In the remaining four preparations, the firing rates were slightly increased or unchanged: between 113.0 and 890.0 imps/min in control and between 123.2 and 1156.0 imps/min at 30-35 min after vehicle injection. The average firing rate was 580.3±127.9 imp/min before vehicle and 513.1±148.3 imps/min after vehicle injection, amounting to 93.9±14.1% of the control level ($P>0.05$, paired student's t-test).

In contrast, in all eight preparations tested ESL, at 100 mg/kg i.p., significantly reduced spontaneous activity of dorsal horn neurones at 30-35 min after administration. The average firing rate was significantly reduced from 378.1±85.4 imps/min in control to 97.5±39.0 imps/min following administration of ESL ($P<0.05$ compared to the vehicle control, Student's t-test). This was equivalent to a reduction in spontaneous activity to 29.5±13.3% of control in the presence of BIA-2-194 ($P<0.01$ compared to the vehicle control, Student's t-test assuming unequal variance). ESL induced inhibition of spontaneous activity after dorsal root sectioning was significantly different from that observed in the vehicle group at 30-35 min after treatment ($P<0.01$, unpaired Student's t-test).

There was no significant difference in the effects of ESL between the different recording preparations ($P>0.05$, Student's t-test for two samples assuming equal variance). However, there was a tendency for ESL to be less effective on spontaneous activity after the dorsal roots were sectioned.

4. Conclusions

ESL, at 100 mg/kg i.p., significantly inhibited ectopic discharge in peripheral nerves of CCI mice. The effects of ESL were similar on ectopic discharge generated either at the neuroma or DRG level. Therefore, it can be concluded that ESL acts at the peripheral level of the nervous system, such as at the neuroma and DRG levels, to inhibit ectopic discharge and reduce neuropathic pain.

ESL, at 100 mg/kg i.p., significantly inhibited spontaneous activity of dorsal horn neurones in CCI mice. The effects of ESL were similar in three CCI preparations with or without spinalisation and following dorsal root section. Therefore, it can be concluded that ESL acts at the level of the central nervous system, spinal cord level, as well as at the level of the peripheral nervous system as shown above.

Study 3—Formalin Paw Test

The method, which detects analgesic activity, follows that described by Wheeler-Aceto et al (see WHEELER-ACETO, H. & A., C. (1991), "Standardization of the rat paw formalin test for the evaluation of analgesics", Psychopharmacology, 104, 35-44). Mice (NMRI) were given an intraplantar injection of 5% formalin (25 µl) into the posterior left paw. This treatment induced paw licking in control animals. The time spent licking was counted for 15 minutes, beginning 15 minutes after injection of formalin. 10 mice were studied per group. The test was performed blind. ESL and carbamazepine (CBZ) were tested at the doses of 10, 30, 100 and 300 mg/kg p.o., and oxcarbazepine (OXC) and R-Lic were tested at the doses of 100 and 300 mg/kg p.o., administered 60 minutes before the test (i.e. 45 minutes before formalin), and compared with a vehicle control group in each experiment. Morphine (64 mg/kg p.o.), administered under the same experimental conditions, was used as reference substance.

Figure 3:
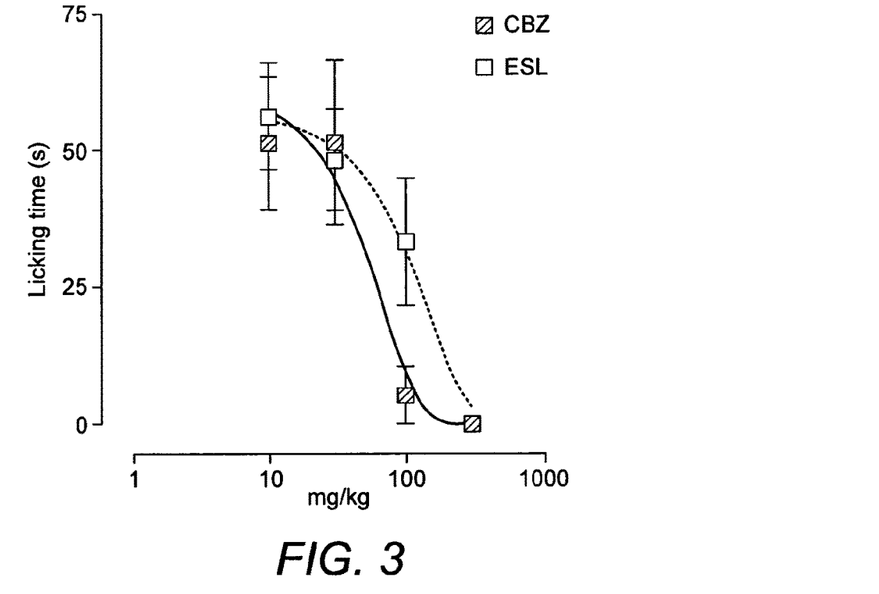
FIG. 3 shows the effect of ESL and carbamazepine (CBZ) on licking time in the formalin paw test in mice. Symbols are means of 10 animals per group; vertical lines indicate S.E.M. values.

FIG. 3 shows the effect of eslicarbazepine acetate (ESL) and carbamazepine (CBZ) on licking time in the formalin paw test in mice. Symbols are means of 10 animals per group; vertical lines indicate S.E.M. values.

Licking time (in seconds) in vehicle-treated mice was 81.0±13.8 (n=10). Both ESL and CBZ reduced licking time in a dose-dependent manner (FIG. 1) with $ED_{50}$ values (in mg/kg) of 69.7 and 38.2, respectively. At 300 mg/kg both compounds abolished licking in the formalin test.

Study 4—Improvement in Quality of Life and Depressive Symptoms Trial 1

During an open label extension of a phase 3 study with ESL, the effect on depressive symptoms in patients taking at least one other anti-epileptic drug was assessed using the Montgomery Åsberg Depression Rating Scale (MADRS) at the end of treatment (after one year or after early discontinuation) and results compared with those at baseline. Patients were treated with ESL dosages in the range of 400-1500 mg, the majority being treated once daily with 800 mg ESL.

Figure 4:
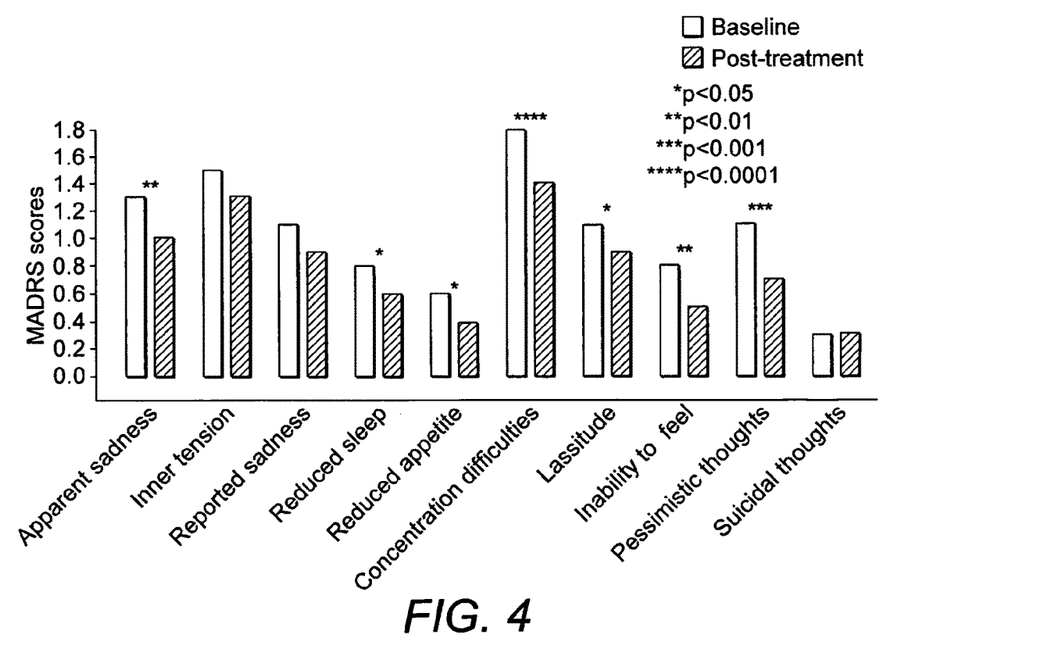
FIG. 4 shows the mean MADRS scores for an ITT population at baseline and at the last assessment of a 1 year treatment or early discontinuations in a phase 3 study. *$p<0.05$, $p<0.01$, *$p<0.001$, ****$p\leq0.0001$

In the intent to treat (ITT) population (166 patients), statistically significant improvements were found in the total score (from 10.5 to 7.8; $p<0.05$), apparent sadness ($p<0.01$), reduced sleep ($p<0.05$), reduced appetite ($p<0.05$), concentration difficulties ($p=0.0001$), lassitude ($p<0.05$), inability to feel ($p<0.01$), and pessimistic thoughts ($p<0.001$) (FIG. 4). In the per-protocol population (108 patients), improvements were seen in the total score ($p<0.0001$), apparent sadness ($p<0.01$), inner tension ($p<0.05$), reported sadness ($p<0.05$), concentration difficulties ($p<0.001$), lassitude ($p<0.05$), inability to feel ($p<0.01$), and pessimistic thoughts ($p<0.001$).

Statistically and clinically significant improvement from baseline was found in quality of life as assessed by MADRS during long-term open-label adjunctive therapy with ESL in partial epilepsy.

Trial 2

During a further open label extension of a phase 3 study with ESL, the effect on depressive symptoms in patients taking at least one other anti-epileptic drug was assessed using the Montgomery Åsberg Depression Rating Scale (MADRS) at the end of treatment (after one year or after early discontinuation) and results compared with those at baseline. Patients were treated with ESL dosages in the range of 400-1500 mg, the majority being treated once daily with 800 mg ESL.

In the ITT population (264 patients), statistically significant improvements were found in the total score ($p<0.0001$), apparent sadness ($p=0.0001$), reported sadness ($p<0.01$), inner tension ($p<0.001$), concentration difficulties ($p<0.0001$), lassitude ($p<0.001$), inability to feel ($p<0.01$), and pessimistic thoughts ($p<0.05$). In the PP population (232 patients), improvements were seen in the total score ($p<0.0001$), apparent sadness ($p<0.0001$), reported sadness ($p<0.01$), inner tension ($p<0.0001$), concentration difficulties ($p<0.0001$), lassitude ($p<0.001$), inability to feel ($p<0.01$), and pessimistic thoughts ($p<0.01$). In the ITT and PP populations, the mean relative improvements were respectively 34% and 38% in apparent sadness, 40% and 41% in reported sadness, 31% and 34% in inner tension, 48% and 53% in reduced sleep, 57% and 62% in reduced appetite, 30% and 33% in concentration difficulties, 38% and 39% in lassitude, 38% and 35% in inability to feel, 26% and 31% in pessimistic thoughts and 56% and 60% in suicidal thoughts.

Depressive mood, as assessed by MADRS, showed statistically significant improvement from baseline during long-term open-label adjunctive therapy with ESL in patients with partial epilepsy.

Study 5—Treatment of Fibromyalgia

Efficacy in the treatment of fibromyalgia is determined in clinical trials in patients meeting the American College of Rheumatology 1990 diagnostic criteria for FMS ((a) 3 or more months of widespread pain (i.e. pain present above and below the waist on the right and left sides of the body and along the midline), and (b) demonstration of pain in at least 11 of 18 specified tender point sites throughout the body when palpated with approximately 4 kg of digital pressure). (Wolfe et al (1990) *Arthritis Rheum* 33(2):160-172). Such trials may be multinational, Phase II, randomised, double-blind, placebo-controlled, parallel-group trials involving placebo medication and dosages such as 400 mg ESL (QD), 800 mg ESL (QD) or 1200 mg ESL (QD). Trials may involve study over a period of time including a titration period and a maintenance treatment period (fixed dose of ESL or placebo).

The efficacy of ESL in treatment of FMS is be measured in terms of the change from baseline to endpoint in mean pain, the 30% responder rate at endpoint, (the proportion of patients with a reduction of endpoint mean pain by at least 30% with respect to baseline), the 30% weekly responder rate (the proportion of patients with a reduction in mean pain per week by at least 30% with respect to baseline), and other secondary efficacy variables based on the pain scores such as 50% responder rates; mean pain intensity per week; fibromyalgia as assessed by the Fibromyalgia Impact Questionnaire (Burckhardt, Clark & Bennett (1991), The Fibromyalia Impact Questionnaire Development and validation, Journal of Rheumatology 18 pp. 728-734); Patient Global Impression of Change (PGIC); Clinician Global Impression of Change (CGIC); depression as assessed by the Montgomery Åsberg Depression Rating Scale (MADRS) (Montgomery & quality of life as assessed by the SF-36 Health Survey; and Asberg (1979) *British Journal of Psychiatry* 134: 382-89); tender point count (Bennett (2005) The Fibromyalgia Impact Questionnaire (FIQ): a review of its development, current version, operating characteristics and uses, Clin. Exp. Rheumatol 23 (Suppl.39) S154-S162); sleep interference as assessed by the Medical Outcome Study (MOS) Sleep Scale (Hays & Stewart (1992) in Stewart & Ware (eds.) Measuring Functioning and Well-being—The Medical Outcomes Study Approach, pp 235-259, Durham N.C., Duke University Press); and intake of rescue medication such as paracetamol.

Pain intensity is assessed by patient questionnaire. The Fibromyalgia Impact Questionnaire involves questions relating to patients ability to perform every day tasks such as shopping, climbing stairs, driving, visiting friends, etc. PGIC and CGIC are determined from the patient's and clinician's respective overall assessment of patient condition.

It will be appreciated that the invention may be modified within the scope of the appended claims.

The invention claimed is:

1. A method for the treatment or management of fibromyalgia, comprising administering a therapeutically effective amount of eslicarbazepine acetate, wherein the eslicarbazepine acetate is administered once-daily in an amount from about 400 mg per day to about 1,600 mg per day, to a patient in need thereof.

2. A method for the treatment or management of fibromyalgia, comprising administering a therapeutically effective amount of at least one compound selected from the group consisting of eslicarbazepine, R-licarbazepine, and a mixture of eslicarbazepine and R-licarbazepine, wherein the eslicarbazepine, the R-licarbazepine, or the mixture of eslicarbazepine and R-licarbazepine is administered once-daily in an amount from about 400 mg per day to about 1,600 mg per day, to a patient in need thereof.

3. The method of claim 1 wherein the compound is administered in an oral dosage form.

4. The method of claim 1 wherein the eslicarbazepine acetate is administered once-daily in the amount of about 400 mg, about 800 mg, or about 1,200 mg per day.

5. A method of treating or managing fibromyalgia comprising administering to a subject a therapeutically effective amount of eslicarbazepine, or a pharmaceutically acceptable salt or solvate thereof, wherein the eslicarbazepine, or a pharmaceutically acceptable salt or solvate thereof, is administered once-daily in an amount from about 400 mg per day to about 1,600 mg per day, to a patient in need thereof.

6. The method of claim 5 wherein the eslicarbazepine, or the pharmaceutically acceptable salt or solvate thereof, is administered once-daily in the amount from about 650 mg to about 1,600 mg.

7. The method of claim 5 wherein the eslicarbazepine, or the pharmaceutically acceptable salt or solvate thereof, is administered once-daily in the amount from about 750 mg to about 1500 mg.

8. The method of claim 2 wherein the wherein the eslicarbazepine, the R-licarbazepine, or the mixture of eslicarbazepine and R-licarbazepine is administered once-daily in the amount of about 400 mg, about 800 mg, or about 1,200 mg per day.

9. The method of claim 5 wherein the eslicarbazepine, or a pharmaceutically acceptable salt or solvate thereof, is administered in an oral dosage form.

10. The method of claim 1, wherein eslicarbazepine acetate is administered in combination with a pharmaceutically acceptable carrier.

11. The method of claim 2 wherein the wherein the eslicarbazepine, the R-licarbazepine, or the mixture of eslicarbazepine and R-licarbazepine, is administered in combination with a pharmaceutically acceptable carrier.

12. A method for the treatment or management of fibromyalgia and partial-onset seizures in the same patient, comprising administering a therapeutically effective amount of eslicarbazepine acetate, wherein the eslicarbazepine acetate is administered once-daily in an amount from about 400 mg per day to about 1,600 mg per day, and wherein the patient suffers from both disorders.

13. The method of claim 12, wherein the eslicarbazepine acetate is administered once-daily in the amount of about 400 mg, about 800 mg, or about 1,200 mg per day.

14. The method of claim 12, wherein the eslicarbazepine acetate is administered in an oral dosage form.

* * * * *